United States Patent
Moujahed et al.

(10) Patent No.: US 11,850,295 B2
(45) Date of Patent: Dec. 26, 2023

(54) ANHYDROUS COMPOSITION COMPRISING A MAGNESIUM SALT

(71) Applicant: L'OREAL, Paris (FR)

(72) Inventors: Zohra Moujahed, Chevilly la Rue (FR); Laure Ramos-Stanbury, Chevilly la Rue (FR); Geraldine Berthault, Chevilly la Rue (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 16/473,939

(22) PCT Filed: Dec. 22, 2017

(86) PCT No.: PCT/EP2017/084560
§ 371 (c)(1),
(2) Date: Jun. 26, 2019

(87) PCT Pub. No.: WO2018/122209
PCT Pub. Date: Jul. 5, 2018

(65) Prior Publication Data
US 2019/0350824 A1  Nov. 21, 2019

(30) Foreign Application Priority Data
Dec. 29, 2016  (FR) ...................................... 1663497

(51) Int. Cl.
| | | |
|---|---|---|
| *A61K 8/19* | (2006.01) | |
| *A61K 8/92* | (2006.01) | |
| *A61K 8/02* | (2006.01) | |
| *A61K 8/04* | (2006.01) | |
| *A61Q 15/00* | (2006.01) | |

(52) U.S. Cl.
CPC .............. *A61K 8/19* (2013.01); *A61K 8/0229* (2013.01); *A61K 8/046* (2013.01); *A61K 8/922* (2013.01); *A61Q 15/00* (2013.01)

(58) Field of Classification Search
CPC ....................................................... A61K 8/29
See application file for complete search history.

(56) References Cited

U.S. PATENT DOCUMENTS

| | | | | |
|---|---|---|---|---|
| 4,659,560 A | * | 4/1987 | Bews .................. | A61K 8/8147 424/47 |
| 5,002,698 A | | 2/1991 | Wirth et al. | |
| 5,236,986 A | | 8/1993 | Sakuta | |
| 5,366,665 A | * | 11/1994 | Cho ...................... | C07C 305/06 424/65 |
| 5,412,004 A | | 5/1995 | Tachibana et al. | |
| 5,783,657 A | | 7/1998 | Pavlin et al. | |
| 5,811,487 A | | 9/1998 | Schulz, Jr. et al. | |
| 5,837,793 A | | 11/1998 | Harashima et al. | |
| 5,874,069 A | | 2/1999 | Mendolia et al. | |
| 5,919,441 A | | 7/1999 | Mendolia et al. | |
| 5,981,680 A | | 11/1999 | Petroff et al. | |
| 6,051,216 A | | 4/2000 | Barr et al. | |
| 6,406,684 B1 | * | 6/2002 | Fecht .................... | A61Q 15/00 424/78.02 |
| 8,545,821 B2 | * | 10/2013 | Maitra ................. | A61K 8/8152 424/63 |
| 2003/0113283 A1 | * | 6/2003 | Mattai .................... | A61K 8/585 424/65 |
| 2012/0014896 A1 | * | 1/2012 | Dombeck .............. | A01N 65/00 424/65 |

FOREIGN PATENT DOCUMENTS

| | | |
|---|---|---|
| DE | 10 2008 012 457 A1 | 12/2008 |
| EP | 0 024 175 A2 | 2/1981 |
| EP | 0 847 752 A1 | 6/1998 |
| FR | 2 792 190 A1 | 10/2000 |
| RU | 2 400 212 C2 | 9/2010 |
| RU | 2 419 413 C2 | 5/2011 |
| WO | WO 92/06778 A1 | 4/1992 |
| WO | WO99/33440 * | 8/1999 |
| WO | WO 02/47619 A2 | 6/2002 |
| WO | WO 02/056847 A1 | 7/2002 |
| WO | WO 2004/024798 A1 | 3/2004 |
| WO | WO/2016/094974 * | 12/2014 |
| WO | WO2015/001271 * | 1/2015 |
| WO | WO2017/119885 * | 1/2016 |
| WO | WO 2016/094974 A1 | 6/2016 |
| WO | WO2016092052 * | 6/2016 |

OTHER PUBLICATIONS

Russian Office Action dated Jan. 31, 2020, in Patent Application No. 2019120130/04, 10 pages (with English translation).
French Preliminary Search Report dated Mar. 21, 2017 in Patent Application No. FR 1663497 (with English translation of categories of cited documents), 3 pages.
International Search Report dated Mar. 14, 2018 in PCT/EP2017/084560 filed Dec. 22, 2017 (with English translation of categories of cited documents), 4 pages.
"Tea Tree Natural Deodorant" Database GNPD, Mintel, XP002768345, Jun. 2016, 2 pages.

* cited by examiner

*Primary Examiner* — Sarah Alawadi
(74) *Attorney, Agent, or Firm* — Oblon, McClelland, Maier & Neustadt, L.L.P.

(57) ABSTRACT

The present invention relates to an anhydrous composition comprising:—at least 0.3% by weight of active material of magnesium salt(s) relative to the total weight of the composition;—at least one hydrocarbon-based plant oil; and—at least one fatty acid ester. The invention also relates to a process for the cosmetic treatment of body odor associated with human perspiration, especially underarm odor, and optionally human perspiration, comprising the step of applying a composition as defined above to a skin surface.

20 Claims, No Drawings

ANHYDROUS COMPOSITION COMPRISING A MAGNESIUM SALT

The present invention relates to the field of compositions, especially cosmetic compositions, preferably deodorant compositions.

More particularly, the invention relates to the field of caring for and cleansing the skin, in particular bodily skin.

The present invention also relates to a process for the cosmetic treatment of the skin, and also to a cosmetic process for treating the body odor associated with human perspiration, especially underarm odor, and optionally human perspiration.

In the cosmetic field, it is known practice to use, in topical application, deodorant products containing active substances of antiperspirant type or of deodorant type to reduce or even eliminate body odor, especially underarm odor, which is generally unpleasant.

Eccrine or apocrine sweat generally has little odor when it is secreted. It is its degradation by bacteria via enzymatic reactions which produces malodorous compounds. Deodorant active agents thus have the function of reducing or preventing the formation of unpleasant odors. This objective can be achieved in particular by means of deodorant and/or antiperspirant activity.

The various systems proposed hitherto may be grouped into major families.

A first family concerns unpleasant-odor absorbers. These absorbers "capture" or reduce the volatility of odorous compounds.

Bactericidal substances are also known, which are preferably selective for the strains responsible for odors, or which limit the growth of bacteria. Among the bactericidal substances which destroy the resident bacterial flora, the one most widely used is Triclosan (2,4,4'-trichloro-2'-hydroxydiphenyl ether). Among the substances which reduce the growth of bacteria, mention may be made of transition-metal chelating agents such as EDTA or DPTA.

Substances that block the enzymatic reactions responsible for the formation of odorous compounds are also known, especially arylsulfatase, 5-lipoxygenase, aminocylase or β-glucuronidase inhibitors.

Deodorant activity may also be obtained by neutralizing the volatile compounds responsible for odor.

Finally, aluminum and/or zirconium salts are also used as antibacterial agents. These salts play a direct role on the deodorant efficacy by reducing the number of bacteria responsible for the degradation of sweat.

However, these various treatments, applied to the skin of the armpits, have a tendency to bring about detrimental changes in the skin.

Deodorant products are generally available in the form of roll-ons, tubes, sticks, aerosols or sprays.

The presentation forms that are the most effective for combating unpleasant odor are alcohol-based presentation forms. However, they have the drawback of causing discomfort at the moment of application, in particular after shaving of the armpit.

Emulsions have the drawback of being wetting and of drying with difficulty under the armpit.

Anhydrous sticks and aerosols are fatty presentation forms that leave a greasy feel under the armpit, and some of which have a tendency to transfer onto clothing, leaving visible and unesthetic marks.

In order especially to overcome the problem of marks, deodorant compositions containing oils with a refractive index close to those of aluminum salts have been developed.

The role of such oils is to reduce the whitish appearance of antiperspirant compositions when they are deposited on the skin and, consequently, to make the marks on clothing less white.

However, such deodorant compositions have the drawback of giving the skin, especially on the armpits, an oily feel that is unpleasant for the user, and do not make it possible to limit the transfer of deodorant products from the skin onto clothing.

There is thus an ongoing need to identify novel methods for treating the body odor associated with human perspiration, especially underarm odor, which do not have the set of drawbacks described above. Treatment methods that can dispense with the use of aluminum salts and/or aluminum and zirconium complexes are nowadays especially sought.

The object of the present invention is especially to meet these expectations.

The invention is more particularly directed toward proposing novel deodorant compositions, which do not require the presence of aluminum salts and which prove to be just as effective.

The aim of the present invention is to satisfy these needs.

Thus, according to a first aspect, the present invention is directed towards an anhydrous composition, especially a cosmetic composition, in particular in aerosol or stick form, comprising:
  at least 0.3% by weight of active material of magnesium salt(s) relative to the total weight of the composition;
  at least one hydrocarbon-based plant oil; and
  at least one fatty acid ester.

Contrary to all expectation, the inventors in fact discovered that a combination of magnesium salt, a hydrocarbon-based plant oil and a fatty acid ester makes it possible to limit the formation of malodorous underarm odors. In addition, the compositions according to the invention can advantageously reduce the tack and produce a dry, non-greasy deposit.

Furthermore, the present invention provides compositions which transfer less onto textiles, thereby generating fewer visible and unesthetic marks on clothing, especially on dark-colored clothing, relative to the compositions already known.

Thus, the compositions, especially the cosmetic compositions, according to the invention have good transfer-resistance and also deodorant properties.

According to a preferred embodiment, the composition according to the invention is in aerosol or stick form.

According to a first preferred aspect, the composition according to the invention is in aerosol form.

According to a second preferred aspect, the composition according to the invention is in stick form.

According to a preferred embodiment, the present invention relates to an anhydrous composition, especially a cosmetic composition, comprising:
  at least 0.3% by weight of active material of magnesium salt(s) relative to the total weight of the composition;
  at least coconut oil; and
  at least one fatty acid ester.

According to another preferred embodiment, the present invention relates to an anhydrous composition, especially a cosmetic composition, comprising:
  at least 0.3% by weight of active material of magnesium salt(s) relative to the total weight of the composition;
  at least one hydrocarbon-based plant oil; and
  at least isopropyl palmitate.

According to yet another preferred embodiment, the present invention relates to an anhydrous composition, especially a cosmetic composition, comprising:
- at least 0.3% by weight of active material of magnesium salt(s) relative to the total weight of the composition;
- at least coconut oil; and
- at least isopropyl palmitate.

According to yet another preferred embodiment, the present invention relates to an anhydrous composition, especially a cosmetic composition, comprising:
- at least 0.3% by weight of active material of magnesium salt(s) relative to the total weight of the composition;
- at least one hydrocarbon-based plant oil; and
- at least one fatty acid ester chosen from isopropyl palmitate, isopropyl myristate, isononyl isononanoate and $C_{12}$-$C_{15}$ alkylbenzoate, and mixtures thereof. According to yet another preferred embodiment, the present invention relates to a composition in anhydrous aerosol form, comprising:
- at least 0.3% by weight of active material of magnesium salt(s) relative to the total weight of the composition;
- at least one hydrocarbon-based plant oil; and
- at least one fatty acid ester.

Moreover, the subject of the present invention is also, according to another of its aspects, the process for the cosmetic treatment of body odor associated with human perspiration, especially underarm odor, and optionally human perspiration, comprising the step of applying a composition as defined above to a skin surface.

The process of the invention is particularly advantageous for treating body odor associated with perspiration under the armpits, since the composition used does not give an unpleasant greasy feel and transfers less onto clothing.

The compositions, especially the cosmetic compositions, according to the invention comprise a physiologically acceptable medium.

For the purposes of the present invention, the term "physiologically acceptable medium" is intended to denote a medium that is suitable for the administration of a composition to the skin.

A physiologically acceptable medium generally has no unpleasant odor or appearance, and is entirely compatible with topical administration to the skin. In the present case, where the composition is intended for application to the surface of the skin, such a medium is considered in particular to be physiologically acceptable when it does not cause any stinging, tautness or redness that is unacceptable to the user.

In particular, the composition is suitable for application to the surface of the skin. Thus, the physiologically acceptable medium is preferentially a cosmetically or dermatologically acceptable medium, i.e. a medium that has no unpleasant odor, color or appearance, and that does not cause the user any unacceptable stinging, tautness or redness.

The composition may then comprise any constituent usually used in the envisaged application.

Needless to say, those skilled in the art will take care to select this or these optional additional compound(s), and/or the amount thereof, such that the advantageous properties of the compounds according to the invention are not, or are not substantially, adversely affected by the envisaged addition.

For the purposes of the present invention, the term "anhydrous" refers to a composition having a water content of less than 5% by weight, in particular less than 2% by weight, preferably less than 1% by weight, or even less than 0.5% by weight, relative to the total weight of the composition. Even more preferentially, a composition according to the invention is totally free of water.

It should be noted that the water that may be present is more particularly bound water, such as water of crystallization in salts, or traces of water absorbed by the starting materials used in the preparation of the compositions of the invention.

Other characteristics, aspects and advantages of the invention will become apparent on reading the detailed description that follows.

Magnesium Salts

A composition according to the invention comprises at least 0.3% by weight of active material of at least one magnesium salt relative to the total weight of the composition. The 0.3% relative to the total composition includes the gas present in the case of an aerosol, i.e. at least 2% relative to the composition as oils.

The magnesium salt is chosen in particular from magnesium oxide, magnesium carbonate, magnesium hydroxide, magnesium bicarbonate, magnesium chloride, magnesium sulfate, magnesium acetate, magnesium pidolate, magnesium gluconate, magnesium glutamate, magnesium heptagluconate, magnesium ketogluconate, magnesium lactate, magnesium ascorbate, magnesium citrate, magnesium aspartate, magnesium pantothenate, magnesium sorbate, magnesium nitrate, magnesium lactate gluconate, magnesium fulvate, and mixtures thereof.

Use will be made more particularly of magnesium oxide, magnesium carbonate, magnesium hydroxide or magnesium bicarbonate, and even more preferentially magnesium oxide.

According to a first embodiment, when the composition according to the invention is in anhydrous aerosol form, the magnesium salts are present in a content ranging from 0.3% to 5% by weight, preferably in a content ranging from 0.5% to 2% by weight of active material, relative to the total weight of the composition.

In particular, when the composition according to the invention is in aerosol form, the proportion of magnesium salts relative to the total weight of the composition (excluding gas) preferably ranges from 2% to 30%, preferably from 3% to 15% by weight.

According to another embodiment, when the composition according to the invention is in stick form, the magnesium salts are present in a content of at least 5% by weight, preferably ranging from 5% to 25% by weight, preferably in a content ranging from 10% to 20% by weight of active material, relative to the total weight of the composition.

In particular, the proportion of magnesium salts relative to the total amount of oils, in a composition according to the invention, especially in stick or aerosol form, ranges in particular from 5% to 30% by weight and preferably from 10% to 25% by weight.

Hydrocarbon-Based Plant Oil

The composition according to the invention, especially in stick or aerosol form, comprises at least one hydrocarbon-based plant oil.

Besides the properties provided to the composition according to the invention, such an oil makes it possible to reduce the white marks that may be left after the application of a deodorant and/or antiperspirant composition.

The hydrocarbon-based plant oil is chosen in particular from liquid triglycerides of fatty acids containing 4 to 24 carbon atoms, for instance heptanoic or octanoic acid triglycerides, or wheatgerm oil, olive oil, sweet almond oil, palm oil, rapeseed oil, coconut oil, cottonseed oil, alfalfa oil, poppy oil, pumpkin oil, marrow oil, blackcurrant oil, evening primrose oil, millet oil, barley oil, quinoa oil, rye oil, safflower oil, candlenut oil, passionflower oil, musk rose oil, sunflower oil, corn oil, soybean oil, grapeseed oil, sesame seed oil, hazelnut oil, apricot oil, macadamia oil, castor oil, avocado oil, caprylic/capric acid triglycerides, for instance those sold by the company Stéarineries Dubois or those sold under the names Miglyol 810, 812 and 818 by the company Dynamit Nobel, jojoba oil and shea butter oil.

Hydrocarbon-based plant oils that may in particular be mentioned include:

coconut oil, derived especially from Cocos nucifera, having a mass per unit volume of between 0.907 and 0.909 g.cm$^{-3}$, a saponification number between 255 and 267, and an iodine number between 5 and 9;

babassu oil (from kernel), derived especially from palm trees, having a mass per unit volume of between 0.914 and 0.917 g.cm$^{-3}$, a saponification number between 245 and 256, and an iodine number between 10 and 18;

palm kernel oil, derived especially from Elaeis guineensis, having a mass per unit volume of between 0.903 and 0.908 g.cm$^{-3}$, a saponification number between 246 and 254, and an iodine number between 12 and 19;

cocoa butter, derived especially from *Theobroma cacao*, having a mass per unit volume of between 0.906 and 0.909 g.cm$^{-3}$, a saponification number between 192 and 200, and an iodine number between 33 and 40;

palm oil (from pulp), derived especially from *Elaeis guineensis*, having a mass per unit volume of between 0.897 and 0.900 g.cm$^{-3}$, a saponification number between 195 and 205, and an iodine number between 45 and 48;

baobab kernel oil, derived especially from *Adansonia grandideris*, having a mass per unit volume of between 0.895 and 0.905 g.cm$^{-3}$, a saponification number between 190 and 195, and an iodine number between 57 and 63;

shea butter derived especially from *Sapotacea multiflora*, having a mass per unit volume of between 0.900 and 0.902 g.cm$^{-3}$, a saponification number between 178 and 193, and an iodine number between 52 and 66;

illipé butter, derived especially from *Skorea stenoptera*, having a mass per unit volume of between 0.902 and 0.905 g.cm$^{-3}$, a saponification number between 190 and 194, and an iodine number between 58 and 65;

olive oil (from pulp and stone), derived especially from *Olea europea*, having a mass per unit volume of between 0.910 and 0.916 g.cm$^{-3}$, a saponification number between 182 and 196, and an iodine number between 75 and 94;

peanut oil, derived especially from *Arachis hypogea*, having a mass per unit volume of between 0.914 and 0.917 g.cm$^{-3}$, a saponification number between 187 and 196, and an iodine number between 80 and 106;

almond oil, derived especially from *Prunus amygdalis*, having a mass per unit volume of between 0.911 and 0.917 g.cm$^{-3}$, a saponification number between 189 and 196, and an iodine number between 95 and 103;

hazelnut oil, derived especially from *Corylu avelana*, having a mass per unit volume of between 0.914 and 0.920 g.cm$^{-3}$, a saponification number between 190 and 195, and an iodine number between 83 and 110;

rapeseed oil, derived especially from *Brassica napus*, having a mass per unit volume of between 0.910 and 0.920 g.cm$^{-3}$, a saponification number between 168 and 181, and an iodine number between 94 and 120; and rice bran oil, derived especially from *Oriza sativa*, having a mass per unit volume of between 0.920 and 0.924 g.cm$^{-3}$, a saponification number between 180 and 194, and an iodine number between 85 and 109.

In particular, a composition according to the invention comprises from 0.5% to 30% by weight of hydrocarbon-based plant oil(s), preferably from 1% to 20% by weight and even more preferentially from 1% to 15% by weight of hydrocarbon-based plant oil(s) relative to the total weight of the composition.

According to a preferred embodiment, the hydrocarbon-based plant oil is chosen from castor oil, sweet almond oil and coconut oil, and mixtures thereof.

Preferably, the hydrocarbon-based plant oil is coconut oil.

Coconut oil is a mixture of various acids, and especially of caproic acid, caprylic acid, capric acid, lauric acid, myristic acid, palmitic acid, stearic acid, oleic acid, linoleic acid and trans fatty acids.

In particular, the proportion of hydrocarbon-based plant oil(s) relative to the total amount of oils ranges from 10% to 90% by weight, preferably from 10% to 50% by weight and even more preferentially from 10% to 35% by weight.

When the composition is in stick form, the proportion of hydrocarbon-based plant oil(s) relative to the total amount of oils ranges in particular from 10% to 40% by weight and preferably from 15% to 35% by weight.

When the composition is in aerosol form, the proportion of hydrocarbon-based plant oil(s) relative to the total amount of oils ranges in particular from 5% to 50% by weight and preferably from 10% to 35% by weight.

Fatty Acid Esters

The composition according to the invention, especially in stick or aerosol form, comprises at least one fatty acid ester.

Fatty acid esters that may especially be mentioned include synthetic fatty acid esters, for instance the oils of formula $R_1COOR_2$ in which $R_1$ represents the residue of a linear or branched higher fatty acid comprising from 1 to 40 carbon atoms and $R_2$ represents a hydrocarbon-based chain, which is especially branched, containing from 1 to 40 carbon atoms, with $R_1+R_2 \geq 10$, for instance purcellin oil (cetostearyl octanoate), isononyl isononanoate, isopropyl myristate, isopropyl palmitate, $C_{12}$ to $C_{15}$ alkyl benzoate, hexyl laurate, diisopropyl adipate, 2-ethylhexyl palmitate, 2-octyldodecyl stearate, 2-octyldodecyl erucate, isostearyl isostearate or tridecyl trimellitate; alcohol or polyalcohol octanoates, decanoates or ricinoleates, for instance propylene glycol dioctanoate; hydroxylated esters, for instance isostearyl lactate, octyl hydroxystearate, octyldodecyl hydroxystearate, diisostearyl malate, triisocetyl citrate, and fatty alcohol heptanoates, octanoates or decanoates; polyol esters, for instance propylene glycol dioctanoate, neopentyl glycol diheptanoate or diethylene glycol diisononanoate; and pentaerythritol esters, for instance pentaerythrityl tetraisostearate.

Preferably, the fatty acid ester is chosen from isopropyl palmitate, isopropyl myristate, isononyl isononanoate and $C_{12}$-$C_{15}$ alkyl benzoate, and mixtures thereof.

Fatty acid esters such as isopropyl palmitate and isopropyl myristate, and mixtures thereof, and even more particularly isopropyl palmitate, will be chosen more preferentially.

In particular, a composition according to the invention, especially in stick or aerosol form, comprises from 1% to 30% by weight of fatty acid ester(s), preferably from 2% to 20% by weight of fatty acid ester(s) and better still from 3% to 15% by weight of fatty acid ester(s) relative to the total weight of the composition.

In particular, the proportion of fatty acid ester(s) relative to the total amount of oils preferably ranges from 10% to 90% by weight, more preferentially from 20% to 80% by weight, preferably from 30% to 60% by weight.

Oily Phase

The composition according to the invention, especially in stick or aerosol form, comprises an oily phase containing at least one hydrocarbon-based plant oil, a fatty acid ester, and optionally one or more oils other than the hydrocarbon-based plant oil and the fatty acid ester.

The term "oil" means a fatty substance that is liquid at room temperature (25° C.) and atmospheric pressure (760 mmHg, i.e. $10^5$ Pa).

Volatile Oil

Advantageously, when the composition according to the invention is in aerosol form, it may comprise at least one volatile oil.

For the purposes of the invention, the term "volatile oil" means an oil that is capable of evaporating on contact with the skin or the keratin fiber in less than one hour, at room temperature and atmospheric pressure.

The volatile oils of the invention are volatile cosmetic oils, which are liquid at room temperature, having a nonzero vapor pressure, at room temperature and atmospheric pressure, ranging in particular from 0.13 Pa to 40 000 Pa ($10^{-3}$ to 300 mmHg), in particular ranging from 1.3 Pa to 13 000 Pa (0.01 to 100 mmHg), and more particularly ranging from 1.3 Pa to 1300 Pa (0.01 to 10 mmHg).

Preferably, the volatile oil is chosen from volatile hydrocarbon-based oils and volatile silicone oils, and mixtures thereof.

As examples of volatile hydrocarbon-based oils that may be used in the invention, mention may be made of volatile hydrocarbon-based oils chosen from hydrocarbon-based oils containing from 8 to 16 carbon atoms, and especially $C_8$-$C_{16}$ isoalkanes of petroleum origin (also known as isoparaffins), such as isododecane (also known as 2,2,4,4,6-pentamethylheptane), isodecane or isohexadecane, for example the oils sold under the Isopar or Permethyl trade names, branched $C_8$-$C_{16}$ esters, isohexyl neopentanoate, and mixtures thereof.

Other volatile hydrocarbon-based oils, for instance petroleum distillates, especially those sold under the name Shell Solt by the company Shell, may also be used, and also volatile linear alkanes, such as those described in patent application DE10 2008 012 457 from the company Cognis.

As examples of volatile silicone oils that may be used in the invention, mention may be made of:

volatile linear or cyclic silicone oils, especially those with a viscosity≤8 centistokes ($8\times10^{-6}$ m$^2$/s) and especially containing from 2 to 7 silicon atoms, these silicones optionally comprising alkyl or alkoxy groups containing from 1 to 10 carbon atoms. As volatile silicone oils that may be used in the invention, mention may be made especially of octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane and dodecamethylpentasiloxane;

volatile linear alkyltrisiloxane oils of general formula (I):

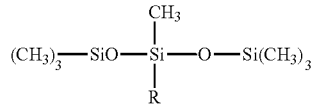

(I)

where R represents an alkyl group comprising from 2 to 4 carbon atoms, one or more hydrogen atoms of which may be replaced with a fluorine or chlorine atom.

Among the oils of general formula (I), mention may be made of:

3-butyl-1,1,1,3,5,5,5-heptamethyltrisiloxane,
3-propyl-1,1,1,3,5,5,5-heptamethyltrisiloxane, and
3-ethyl-1,1,1,3,5,5,5-heptamethyltrisiloxane, corresponding to the oils of formula (I) for which R is, respectively, a butyl group, a propyl group or an ethyl group.

When the composition is in aerosol form, the proportion of volatile oil(s) relative to the total amount of oils preferably ranges from 10% to 90% by weight and preferably from 15% to 85% by weight.

Preferably, the volatile oils are chosen from hydrocarbon-based oils and more particularly $C_8$-$C_{16}$ isoalkanes such as isododecane or isohexadecane, or linear $C_8$-$C_{16}$ alkanes such as an undecane/tridecane mixture.

Even more particularly, isododecane will be chosen.

When the composition according to the invention is in anhydrous aerosol form, the proportion of volatile oil(s) relative to the total amount of oils preferably ranges from 20% to 80% by weight.

Nonvolatile Oil

The composition according to the invention, especially in stick or aerosol form, may also comprise at least one nonvolatile oil, other than the fatty acid ester(s) and the hydrocarbon-based plant oil(s) already present in the composition.

The term "nonvolatile oil" means an oil that remains on the skin or the keratin fiber at room temperature and atmospheric pressure for at least several hours, and that especially has a vapor pressure strictly less than $10^{-3}$ mmHg (0.13 Pa).

The nonvolatile oil may be chosen from nonvolatile hydrocarbon-based oils, nonvolatile silicone oils and nonvolatile fluoro oils, and mixtures thereof.

The term "hydrocarbon-based oil" means an oil mainly containing carbon and hydrogen atoms and possibly one or more functions chosen from hydroxyl, ester, ether and carboxylic functions. Generally, the oil has a viscosity of from 0.5 to 100 000 mPa.s, preferably from 50 to 50 000 mPa.s and more preferably from 100 to 30 000 mPa.s.

As examples of nonvolatile hydrocarbon-based oils that may be used in the invention, mention may be made of:

linear or branched hydrocarbons, of mineral or synthetic origin, such as liquid paraffins and derivatives thereof, petroleum jelly, polydecenes, polybutenes, hydrogenated polyisobutene such as Parleam®, or squalane;

synthetic ethers containing from 10 to 40 carbon atoms, such as dicaprylyl ether or PPG-14 butyl ether;

fatty alcohols that are liquid at room temperature, containing a branched and/or unsaturated carbon chain containing from 12 to 26 carbon atoms, for instance octyldodecanol, isostearyl alcohol, 2-butyloctanol, 2-hexyldecanol, 2-undecylpentadecanol or oleyl alcohol;

higher fatty acids such as oleic acid, linoleic acid or linolenic acid;

fatty-chain carbonates;

fatty-chain acetates;

fatty-chain citrates.

As examples of nonvolatile silicone oils that may be used in the invention, mention may be made of silicone oils such as linear or cyclic nonvolatile polydimethylsiloxanes (PDMSs), polydimethylsiloxanes comprising alkyl, alkoxy or phenyl groups, which are on the side or at the end of a silicone chain, these groups especially containing from 2 to 24 carbon atoms; and mixtures thereof.

As examples of nonvolatile fluoro oils that may be used in the invention, mention may be made of optionally partially hydrocarbon-based and/or silicone-based fluoro oils, such as fluorosilicone oils, fluorinated polyethers and fluorosilicones as described in EP 847 752.

Preferably, the nonvolatile oils are chosen from nonvolatile hydrocarbon-based oils and more particularly hydrogenated polyisobutene oils such as Parleam®, ethers such as dicaprylyl ether or PPG-14 butyl ether, fatty alcohols such as octyldodecanol, and mixtures thereof.

In particular, when the composition according to the invention is in anhydrous aerosol form, the proportion of volatile oil(s) relative to the total amount of oils preferably ranges from 10% to 90% by weight and more preferentially from 15% to 80% by weight.

In particular, when the composition according to the invention is in stick form, it comprises 100% of nonvolatile oil(s) relative to the total amount of oils.

Solid Fatty Substances

According to a particular embodiment of the invention, when the composition is in stick form, it may comprise at least one solid fatty substance preferably chosen from waxes and pasty fatty substances, and mixtures thereof, and more particularly waxes.

Pasty Fatty Substance

For the purposes of the present invention, the term "pasty fatty substance" (also known as "pasty compound" or "paste") means a lipophilic fatty compound with a reversible solid/liquid change of state, displaying anisotropic crystal organization in the solid state, and comprising a liquid fraction and a solid fraction at a temperature of 23° C.

In other words, the starting melting point of the pasty compound may be less than 23° C. The liquid fraction of the pasty compound measured at 23° C. may represent 9% to 97% by weight of the compound. This fraction that is liquid at 23° C. preferably represents between 15% and 85% and more preferably between 40% and 85% by weight. For the purposes of the invention, the melting temperature corresponds to the temperature of the most endothermic peak observed on thermal analysis (DSC) as described in standard ISO 11357-3:1999. The melting point of a pasty substance or of a wax may be measured using a differential scanning calorimeter (DSC), for example the calorimeter sold under the name MDSC 2920 by the company 45 TA Instruments.

The measuring protocol is as follows: a sample of 5 mg of pasty substance or wax (depending on the case) placed in a crucible is subjected to a first temperature rise ranging from −20° C. to 100° C., at a heating rate of 10° C./minute, is then cooled from 100° C. to −20° C. at a cooling rate of 10° C./minute and is finally subjected to a second temperature rise ranging from −20° C. to 100° C. at a heating rate of 5° C./minute. During the second temperature rise, the variation in the difference between the power absorbed by the empty crucible and by the crucible containing the sample of pasty substance or wax as a function of the temperature is measured.

The melting point of the compound is the temperature value corresponding to the top of the peak of the curve representing the variation in the difference in power absorbed as a function of the temperature.

The liquid fraction by weight of the pasty compound at 23° C. is equal to the ratio of the heat of fusion consumed at 23° C. to the heat of fusion of the pasty compound.

The heat of fusion of the pasty compound is the heat consumed by the compound in order to pass from the solid state to the liquid state. The pasty compound is said to be in the solid state when all of its mass is in crystalline solid form. The pasty compound is said to be in the liquid state when all of its mass is in liquid form.

The heat of fusion of the pasty compound is equal to the area under the curve of the thermogram obtained using a differential scanning calorimeter (DSC), such as the calorimeter sold under the name MDSC 2920 by the company TA Instruments, with a temperature rise of 5° C. or 10° C. per minute, according to standard ISO 11357-3:1999. The heat of fusion of the pasty compound is the amount of energy required to make the compound change from the solid state to the liquid state. It is expressed in J/g. The heat of fusion consumed at 23° C. is the amount of energy absorbed by the sample to change from the solid state to the state that it has at 23° C., formed from a liquid fraction and a solid fraction.

The liquid fraction of the pasty compound measured at 32° C. preferably represents from 30% to 100% by weight of the compound, preferably from 50% to 100% and more preferably from 60% to 100% by weight of the compound. When the liquid fraction of the pasty compound measured at 32° C. is equal to 100%, the temperature of the end of the melting range of the pasty compound is less than or equal to 32° C.

The liquid fraction of the pasty compound measured at 32° C. is equal to the ratio of the heat of fusion consumed at 32° C. to the heat of fusion of the pasty compound. The heat of fusion consumed at 32° C. is calculated in the same way as the heat of fusion consumed at 23° C.

The pasty compound is preferably chosen from synthetic compounds and compounds of plant origin. A pasty compound may be obtained by synthesis from starting materials of plant origin. The pasty compound is advantageously chosen from:

lanolin and derivatives thereof;
polyol ethers chosen from ethers of pentaerythritol and of polyalkylene glycol, ethers of fatty alcohol and of sugar, and mixtures thereof, the ethers of pentaerythritol and of polyethylene glycol comprising 5 oxyethylene units (5 OE) (CTFA name: PEG-5 Pentaerythrityl Ether), the polypropylene glycol pentaerythrityl ether comprising 5 oxypropylene (5 OP) units (CTFA name: PPG-5 Pentaerythrityl Ether) and mixtures thereof, and more especially the mixture PEG-5 Pentaerythrityl Ether, PPG-5 Pentaerythrityl Ether and soybean oil, sold under the name Lanolide by the company Vevy, which is a mixture in which the constituents are in a 46/46/8 weight ratio: 46% PEG-5 pentaerythrityl ether, 46% PPG-5 pentaerythrityl ether and 8% soybean oil;
polymeric or non-polymeric silicone compounds;
polymeric or non-polymeric fluoro compounds;
vinyl polymers, especially olefin homopolymers and copolymers, hydrogenated diene homopolymers and copolymers, linear or branched oligomers, homopolymers or copolymers of alkyl (meth)acrylates preferably containing a $C_8$-$C_{30}$ alkyl group, homopolymer and copolymer oligomers of vinyl esters containing $C_8$-$C_{30}$ alkyl groups, homopolymer and copolymer oligomers of vinyl ethers containing $C_8$-$C_{30}$ alkyl groups;
liposoluble polyethers resulting from polyetherification between one or more $C_2$-$C_{100}$ and preferably $C_2$-$C_{50}$ diols;
esters;
and/or mixtures thereof.

The pasty compound is preferably a polymer, especially a hydrocarbon-based polymer.

Among the liposoluble polyethers that are particularly preferred are copolymers of ethylene oxide and/or of propylene oxide with $C_6$-$C_{30}$ long-chain alkylene oxides, more preferably such that the weight ratio of the ethylene oxide and/or of the propylene oxide to the alkylene oxides in the copolymer is from 5:95 to 70:30.

In this family, mention will be made especially of copolymers such as long-chain alkylene oxides arranged in blocks with an average molecular weight from 1000 to 10 000, for example a polyoxyethylene/polydodecyl glycol block copolymer such as the ethers of dodecanediol (22 mol) and of polyethylene glycol (45 OE) sold under the brand name Elfacos ST9 by Akzo Nobel.

Among the esters, the following are in particular preferred:
  esters of a glycerol oligomer, especially diglycerol esters, in particular condensates of adipic acid and of glycerol, for which some of the hydroxyl groups of the glycerols have reacted with a mixture of fatty acids such as stearic acid, capric acid, stearic acid and isostearic acid, and 12-hydroxystearic acid, especially such as those sold under the brand name Softisan 649 by the company Sasol;
  the arachidyl propionate sold under the brand name Waxenol 801 by Alzo;
  phytosterol esters;
  fatty acid triglycerides and derivatives thereof;
  pentaerythritol esters;
  non-crosslinked polyesters resulting from polycondensation between a linear or branched $C_4$-$C_{50}$ dicarboxylic acid or polycarboxylic acid and a $C_2$-$C_{50}$ diol or polyol,
  ester aliphatic esters resulting from the esterification of an aliphatic hydroxycarboxylic acid ester with an aliphatic carboxylic acid. Preferably, the aliphatic carboxylic acid comprises from 4 to 30 and preferably from 8 to 30 carbon atoms. It is preferably chosen from hexanoic acid, heptanoic acid, octanoic acid, 2-ethylhexanoic acid, nonanoic acid, decanoic acid, undecanoic acid, dodecanoic acid, tridecanoic acid, tetradecanoic acid, pentadecanoic acid, hexadecanoic acid, hexyldecanoic acid, heptadecanoic acid, octadecanoic acid, isostearic acid, nonadecanoic acid, eicosanoic acid, isoarachidic acid, octyldodecanoic acid, heneicosanoic acid and docosanoic acid, and mixtures thereof. The aliphatic carboxylic acid is preferably branched. The aliphatic hydroxycarboxylic acid ester is advantageously derived from a hydroxylated aliphatic carboxylic acid comprising from 2 to 40 carbon atoms, preferably from 10 to 34 carbon atoms and better still from 12 to 28 carbon atoms, and from 1 to 20 hydroxyl groups, preferably from 1 to 10 hydroxyl groups and better still from 1 to 6 hydroxyl groups.

The aliphatic hydroxycarboxylic acid ester is chosen from:
  a) partial or total esters of saturated linear monohydroxylated aliphatic monocarboxylic acids;
  b) partial or total esters of unsaturated monohydroxylated aliphatic monocarboxylic acids;
  c) partial or total esters of saturated monohydroxylated aliphatic polycarboxylic acids;
  d) partial or total esters of saturated polyhydroxylated aliphatic polycarboxylic acids;
  e) partial or total esters of $C_2$ to $C_{16}$ aliphatic polyols that have reacted with a monohydroxylated or polyhydroxylated aliphatic monocarboxylic or polycarboxylic acid, and mixtures thereof;
  esters of a diol dimer and of a diacid dimer, where appropriate esterified on their free alcohol or acid function(s) with acid or alcohol radicals, especially dimer dilinoleate esters; such esters may be chosen especially from the esters having the following INCI nomenclature: bis-behenyl/isostearyl/phytosteryl dimer dilinoleyl dimer dilinoleate (Plandool G), phytosteryl/isostearyl/cetyl/stearyl/behenyl dimer dilinoleate (Plandool H or Plandool 40 S), and mixtures thereof;
  hydrogenated rosinate esters, such as dilinoleyl dimers of hydrogenated rosinate (Lusplan DD-DHR or DD-DHR from Nippon Fine Chemical); and
  mixtures thereof.

Waxes

According to a preferred embodiment, when the composition according to the invention is in stick form, it comprises at least one wax.

The wax under consideration in the context of the present invention is generally a lipophilic compound that is solid at room temperature (25° C.), with a solid/liquid reversible change of state, having a melting point of greater than or equal to 30° C., which may be up to 200° C. and in particular up to 120° C. In particular, the waxes that are suitable for use in the invention may have a melting point of greater than or equal to 45° C., and in particular greater than or equal to 55° C. The waxes that may be used in the compositions according to the invention are chosen from waxes that are solid at room temperature, of animal, plant, mineral or synthetic origin, and mixtures thereof.

Examples that may be mentioned include the following hydrocarbon-based waxes comprising a fatty alkyl chain generally containing from 10 to 60 carbon atoms and preferably from 20 to 40 carbon atoms, said chain possibly being saturated or unsaturated, substituted or unsubstituted, and linear, branched or cyclic, preferably saturated and linear:
  fatty alcohols;
  fatty alcohol esters;
  fatty acids;
  fatty acid amides;
  fatty acid esters including triglycerides;
  fatty acid ethers;
  ethoxylated fatty alcohols;
  ethoxylated fatty acids and the corresponding salts thereof.

Among the fatty alcohols, mention may be made of stearyl alcohol and cetearyl alcohol, or mixtures thereof.

Among the fatty alcohol esters, mention may be made of triisostearyl citrate, ethylene glycol bis(12-hydroxystearate), tristearyl citrate, stearyl octanoate, stearyl heptanoate, trilauryl citrate, and mixtures thereof. Among the fatty acid esters, mention may be made of ester waxes, monoglycerides, diglycerides and triglycerides.

Ester waxes that may be mentioned include stearyl stearate, stearyl behenate, stearyloctyldodecanol, cetearyl behenate, behenyl behenate, ethylene glycol distearate and ethylene glycol dipalmitate. Use may be made in particular of a $C_{20}$-$C_{40}$ alkyl (hydroxystearyloxy)stearate (the alkyl group containing from 20 to 40 carbon atoms), alone or as a mixture.

Such a wax is especially sold under the names Kester Wax K 82 P®, Hydroxypolyester K 82 P® and Kester Wax K 80 P® by the company Koster Keunen.

Among the triglyceride waxes, mention may be made more particularly of tribehenin, $C_{18}$-$C_{36}$ triglycerides, and mixtures thereof.

As illustrations of waxes that are suitable for the invention, mention may be made especially of hydrocarbon-based waxes, for instance beeswax, lanolin wax, Chinese insect waxes, rice bran wax, carnauba wax, candelilla wax, ouricury wax, esparto grass wax, berry wax, shellac wax, Japan wax and sumach wax; montan wax, orange wax and lemon wax, microcrystalline waxes, paraffins and ozokerite; polyethylene waxes, the waxes obtained by Fischer-Tropsch synthesis and waxy copolymers, and also esters thereof.

Mention may also be made of waxes obtained by catalytic hydrogenation of animal or plant oils containing linear or branched $C_8$-$C_{32}$ fatty chains. Among these, mention may be made especially of isomerized jojoba oil such as the trans-isomerized partially hydrogenated jojoba oil manufactured or sold by the company Desert Whale under the trade reference Iso-Jojoba-50®, hydrogenated sunflower oil, hydrogenated castor oil, hydrogenated coconut oil, hydrogenated lanolin oil, and the bis(1,1,1-trimethylolpropane) tetrastearate sold under the name Hest 2T-4S® by the company Heterene.

Mention may also be made of silicone waxes ($C_{30-45}$ alkyl dimethicone) and fluorinated waxes. The waxes obtained by hydrogenation of castor oil esterified with cetyl alcohol, sold under the names Phytowax ricin 16L64® and 22L73® by the company Sophim, may also be used. Such waxes are especially described in patent application FR 2 792 190.

As microwaxes that may be used in the compositions according to the invention, mention may be made especially of carnauba microwaxes such as the product sold under the name MicroCare 350® by the company Micro Powders, synthetic microwaxes such as the product sold under the name MicroEase 114S® by the company Micro Powders, microwaxes formed from a mixture of carnauba wax and polyethylene wax, such as those sold under the names MicroCare 300® and 310® by the company Micro Powders, microwaxes formed from a mixture of carnauba wax and synthetic wax, such as the product sold under the name MicroCare 325® by the company Micro Powders, polyethylene microwaxes such as those sold under the names Micropoly 200®, 220®, 220L® and 250S® by the company Micro Powders, and polytetrafluoroethylene microwaxes such as those sold under the names Microslip 519® and 519 L® by the company Micro Powders.

According to a particular embodiment according to the invention, when the composition is in stick form, the composition according to the invention may comprise a content of solid fatty substance preferably ranging from 1% to 30% by weight, in particular from 2% to 25% by weight and more particularly from 5% to 20% by weight, relative to the total weight of the composition.

Additives

The cosmetic compositions according to the invention, especially in stick or aerosol form, may also comprise cosmetic adjuvants chosen from deodorant active agents, moisture absorbers, lipophilic suspension agents or gelling agents, softeners, antioxidants, opacifiers, stabilizers, moisturizers, vitamins, bactericides, preserving agents, polymers, fragrances, thickeners or suspension agents or any other ingredient usually used in cosmetics for this type of application.

The composition according to the invention may also comprise lipophilic thickeners, gelling agents and/or suspension agents to improve the texture or the homogeneity of the products.

Needless to say, a person skilled in the art will take care to select this or these optional additional compounds such that the advantageous properties intrinsically associated with the composition in accordance with the invention are not, or are not substantially, adversely affected by the envisaged addition(s).

Deodorant Active Agents

According to a particular form of the invention, the compositions, especially in stick or aerosol form, may contain at least one deodorant active agent in the liquid phase, other than the magnesium salts considered previously.

The term "deodorant active agent" means any substance that is capable of reducing, masking or absorbing human body odor, in particular underarm odor.

The deodorant active agents may be bacteriostatic agents or bactericidal agents that act on the microorganisms of underarm odor, such as 2,4,4'-trichloro-2'-hydroxydiphenyl ether (Triclosan®), 2,4-dichloro-2'-hydroxydiphenyl ether, 3',4',5'-trichlorosalicylanilide, 1-(3',4'-dichlorophenyl)-3-(4'-chlorophenyl)urea (Triclocarban®) or 3,7,11-trimethyl-dodeca-2,5,10-trienol (Farnesol®); quaternary ammonium salts such as cetyltrimethylammonium salts, cetylpyridinium salts, DPTA (1,3-diaminopropanetetraacetic acid), 1,2-decanediol (Symclariol from the company Symrise); glycerol derivatives, for instance caprylic/capric glycerides (Capmul MCM® from Abitec), glyceryl caprylate or caprate (Dermosoft GMCY® and Dermosoft GMC® from Straetmans), polyglyceryl-2 caprate (Dermosoft DGMC® from Straetmans), and biguanide derivatives, for instance polyhexamethylene biguanide salts; chlorhexidine and salts thereof; 4-phenyl-4,4-dimethyl-2-butanol (Symdeo MPP® from Symrise); zinc salts such as zinc salicylate, zinc gluconate, zinc pidolate, zinc sulfate, zinc chloride, zinc lactate or zinc phenolsulfonate; salicylic acid and derivatives thereof such as 5-n-octanoylsalicylic acid.

The deodorant active agents may be odor absorbers such as zinc ricinoleates, sodium bicarbonate; metallic or silver or silver-free zeolites, or cyclodextrins and derivatives thereof.

They may also be chelating agents such as Dissolvine GL-47-S® from Akzo Nobel, EDTA and DPTA. It may also be a polyol such as glycerol or 1,3-propanediol (Zemea Propanediol sold by Dupont Tate and Lyle BioProducts); or also an enzyme inhibitor such as triethyl citrate; or alum.

The deodorant active agents may also be bacteriostatic agents or bactericidal agents, 2,4,4'-trichloro-2'-hydroxydiphenyl ether (Triclosan®), 2,4-dichloro-2'-hydroxydiphenyl ether, 3',4',5'-trichlorosalicylanilide, 1-(3',4'-dichlorophenyl)-3-(4'-chlorophenyl)urea (Triclocarban®) or 3,7,11-trimethyldodeca-2,5,10-trienol (Farnesol®); quaternary ammonium salts such as cetyltrimethylammonium salts or cetylpyridinium salts.

The deodorant active agents may be present in the composition according to the invention in a proportion of approximately 0.01% to 20% by weight relative to the total composition, and preferably in a proportion of approximately 0.1% to 5% by weight relative to the total weight of the composition.

Moisture Absorbers

It is also possible to add moisture absorbers, for instance perlites and preferably expanded perlites.

The cosmetic composition, especially in stick or aerosol form, may comprise one or more moisture absorbers chosen from perlites.

Preferably, the cosmetic composition comprises one or more absorbers chosen from expanded perlites.

The perlites that may be used according to the invention are generally aluminosilicates of volcanic origin and have as the composition:

70.0-75.0% by weight of silica $SiO_2$;
12.0-15.0% by weight of aluminum oxide $Al_2O_3$;
3.0-5.0% of sodium oxide $Na_2O$;
3.0-5.0% of potassium oxide $K_2O$;
0.5-2% of iron oxide $Fe_2O_3$;
0.2-0.7% of magnesium oxide MgO;
0.5-1.5% of calcium oxide CaO; and
0.05-0.15% of titanium oxide $TiO_2$.

The perlite is ground, dried and then sized in a first step. The product obtained, known as perlite ore, is gray-colored and has a size of about 100 μm.

The perlite ore is then expanded (1000° C./2 seconds) to give more or less white particles. When the temperature reaches 850-900° C., the water trapped in the structure of the material evaporates and brings about the expansion of the material, relative to its original volume. The expanded perlite particles in accordance with the invention may be obtained via the expansion process described in patent U.S. Pat. No. 5,002,698.

Preferably, the perlite particles used will be ground; in this case, they are known as Expanded Milled Perlite (EMP). They preferably have a particle size defined by a median diameter D50 ranging from 0.5 to 50 gm and preferably from 0.5 to 40 μm. Preferably, the perlite particles used have an untamped apparent density at 25° C. ranging from 10 to 400 kg/m³ (standard DIN 53468) and preferably from 10 to 300 kg/m³.

Preferably, the expanded perlite particles according to the invention have a water absorption capacity, measured at the wet point, ranging from 200% to 1500% and preferably from 250% to 800%.

The wet point corresponds to the amount of water which has to be added to 1 g of particle in order to obtain a homogeneous paste. This method derives directly from the oil uptake method applied to solvents. The measurements are taken in the same manner by means of the wet point and the flow point, which have, respectively, the following definition: wet point: weight expressed in grams per 100 g of product corresponding to the production of a homogeneous paste during the addition of a solvent to a powder. flow point: weight expressed in grams per 100 g of product at and above which the amount of solvent is greater than the capacity of the powder to retain it. This is reflected by the production of a more or less homogeneous mixture which flows over the glass plate.

The wet point and the flow point are measured according to the following protocol:

Protocol for Measuring the Water Absorption
1) Equipment Used
Glass plate (25×25 mm)
Spatula (wooden shaft and metal part (15×2.7 mm))
Silk-bristled brush
Balance
12) Procedure The glass plate is placed on the balance and 1 g of perlite particles is weighed out. The beaker containing the solvent and the liquid sampling pipette is placed on the balance. The solvent is gradually added to the powder, the whole being regularly blended (every 3 to 4 drops) by means of the spatula.

The weight of solvent needed to obtain the wet point is noted. Further solvent is added and the weight which makes it possible to reach the flow point is noted. The average of three tests will be determined.

The expanded perlite particles sold under the trade names Optimat 1430 OR or Optimat 2550 by the company World Minerals will be used in particular.

Mineral Thickeners, Gelling Agents and Suspension Agents

As lipophilic mineral thickener, gelling agent or suspension agent, use may be made of modified clays that are preferably chosen from hydrophobic-modified montmorillonite clays, for instance hydrophobic-modified bentonites or hectorites. Examples that may be mentioned include the product Stearalkonium Bentonite (CTFA name) (product of reaction of bentonite and the quaternary ammonium stearalkonium chloride) such as the commercial product sold under the name Tixogel MP 250 by the company Sud Chemie Rheologicals, United Catalysts Inc. or the product Disteardimonium Hectorite (CTFA name) (product of reaction of hectorite and distearyldimonium chloride) sold under the name Bentone 38 or Bentone Gel by the company Elementis Specialities.

Mention may also be made of fumed silica optionally subjected to a hydrophobic surface treatment, the particle size of which is less than 1 μm. This is because it is possible to chemically modify the surface of the silica, by chemical reaction generating a reduction in the number of silanol groups present at the surface of the silica. It is especially possible to substitute silanol groups with hydrophobic groups: a hydrophobic silica is then obtained. The hydrophobic groups may be trimethylsiloxyl groups, which are obtained especially by treating fumed silica in the presence of hexamethyldisilazane. Silicas thus treated are known as "silica silylate" according to the CTFA (8th Edition, 2000). They are sold, for example, under the references Aerosil R812® by the company Degussa, Cab-O-Sil TS-530® by the company Cabot, dimethylsilyloxyl or polydimethylsiloxane groups, which are obtained especially by treating fumed silica in the presence of polydimethylsiloxane or dimethyldichlorosilane. Silicas thus treated are known as "Silica Dimethyl Silylate" according to the CTFA (8th Edition, 2000). They are sold, for example, under the references Aerosil R972® and Aerosil R974® by the company Degussa and Cab-O-Sil TS-610® and Cab-O-Sil TS-720® by the company Cabot.

The hydrophobic fumed silica preferably has a particle size that may be nanometric to micrometric, for example ranging from about 5 to 200 nm.

Organic Thickeners, Gelling Agents and Suspension Agents

The organic lipophilic thickeners or gelling agents are, for example, partially or totally crosslinked elastomeric organopolysiloxanes of three-dimensional structure, for instance those sold under the names KSG6®, KSG16® and KSG18® by the company Shin-Etsu, Trefil E-505C® or Trefil E-506C® by the company Dow Corning, Gransil SR-CYC®, SR DMF10®, SR-DC556®, SR 5CYC gel®, SR DMF 10 gel® and SR DC 556 gel® by the company Grant Industries and SF 1204® and JK 113® by the company General Electric; ethylcellulose, for instance the product sold under the name Ethocel® by the company Dow Chemical; galactomannans comprising from one to six and in particular from two to four hydroxyl groups per saccharide, substituted with a saturated or unsaturated alkyl chain, for instance guar gum alkylated with $C_1$ to $C_6$, and in particular $C_1$ to $C_3$, alkyl chains, and mixtures thereof; block copolymers of "diblock", "triblock" or "radial" type, of the polystyrene/polyisoprene or polystyrene/polybutadiene type, such as the products sold under the name Luvitol HSB® by the company BASF, of the polystyrene/copoly (ethylene-propylene) type, such as the products sold under the name Kraton® by the company Shell Chemical Co., or of the polystyrene/copoly(ethylene-butylene) type, and mixtures of triblock and radial (star) copolymers in isododecane, such as those sold by the company Penreco under the name Versagel®, for instance the mixture of butylene/ethylene/styrene triblock copolymer and of ethylene/propylene/styrene star copolymer in isododecane (Versagel M 5960).

Lipophilic thickeners or gelling agents that may also be mentioned include polymers with a weight-average molecular mass of less than 100 000, comprising a) a polymer backbone with hydrocarbon-based repeating units containing at least one heteroatom, and optionally b) at least one optionally functionalized pendent fatty chain and/or terminal fatty chain, containing from 6 to 120 carbon atoms and being linked to these hydrocarbon-based units, as described in patent applications WO-A02/056 847 and WO-A02/47619, in particular polyamide resins (especially comprising alkyl groups containing from 12 to 22 carbon atoms) such as those described in US-A-5 783 657.

Among the lipophilic thickeners or gelling agents that may be used in the compositions according to the invention, mention may also be made of fatty acid esters of dextrin, such as dextrin palmitates, especially such as the products sold under the name Rheopearl TL® or Rheopearl KL® by the company Chiba Flour.

It is also possible to use silicone polyamides of the polyorganosiloxane type such as those described in documents U.S. Pat. Nos. 5,874,069, 5,919,441, 6,051,216 and 5,981,680.

These silicone polymers may belong to the following two families:
polyorganosiloxanes comprising at least two groups capable of establishing hydrogen interactions, these two groups being in the chain of the polymer, and/or
polyorganosiloxanes comprising at least two groups capable of establishing hydrogen interactions, these two groups being located on grafts or branches.

The thickening agents, gelling agents and/or suspending agents are preferably present in amounts ranging from 0.1% to 15% by weight and more preferentially from 0.2% to 10% by weight relative to the total weight of the composition.

The amounts of these various constituents that may be present in the composition according to the invention are those conventionally used in compositions for treating perspiration.

Emulsifiers

The oily phase may also contain one or more emulsifiers with an HLB (hydrophilic/lipophilic balance) of less than 8, preferably less than or equal to 6 and especially ranging from 4 to 6.

They may be soluble or dispersible in said phase.

Examples of emulsifiers that may be mentioned include fatty esters of polyols, especially of glycerol or sorbitol, and especially the isostearic, oleic and ricinoleate esters of polyols, such as the mixture of petrolatum, polyglyceryl-3 oleate, glyceryl isostearate, hydrogenated castor oil and ozokerite, sold under the name Protegin W® by the company Goldschmidt, sorbitan isostearate, polyglyceryl diisostearate, polyglyceryl-2 sesquiisostearate; saccharide esters and ethers such as methyl glucose dioleate; fatty esters such as magnesium lanolate; dimethicone copolyols and alkyl dimethicone copolyols. Examples that may be mentioned include the alkyl dimethicone copolyols corresponding to formula (I) below:

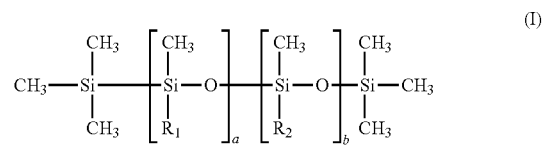

in which:
$R_1$ denotes a linear or branched $C_{12}$-$C_{20}$ and preferably $C_{12}$-$C_{18}$ alkyl group;
$R_2$ denotes the group: $-C_nH_{2n}-(-OC_2H_4-)_x-(-OC_3H_6-)_y-O-R_3$;
$R_3$ denotes a hydrogen atom or a linear or branched alkyl radical comprising from 1 to 12 carbon atoms;
a is an integer ranging from 1 to 500 approximately;
b is an integer ranging from 1 to 500 approximately;
n is an integer ranging from 2 to 12 and preferably from 2 to 5;
x is an integer ranging from 1 to 50 approximately and preferably from 1 to 30;
y denotes an integer ranging from 0 to 49 approximately and preferably from 0 to 29, with the proviso that when y is other than zero, the ratio x/y is greater than 1 and preferably ranges from 2 to 11.

Among the alkyl dimethicone copolyol emulsifiers of formula (I) that are preferred, mention will be made more particularly of Cetyl PEG/PPG-10/1 Dimethicone and more particularly the mixture Cetyl PEG/PPG-10/1 Dimethicone and Dimethicone (INCI name), for instance the product sold under the trade name Abil EM90 by the company Goldschmidt, or alternatively the mixture (Polyglyceryl-4 Stearate and Cetyl PEG/PPG-10 (and) Dimethicone (and) Hexyl Laurate), for instance the product sold under the trade name Abil WE09 by the same company.

Among the water-in-oil emulsifiers, mention may also be made of the dimethicone copolyols corresponding to formula (II) below:

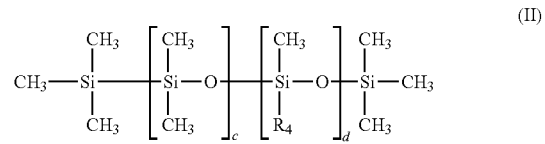

in which:
$R_4$ denotes the group: $-C_mH_{2m}-(-OC_2H_4-)_s-(-OC_3H_6-)_t-O-R_5$;
$R_5$ denotes a hydrogen atom or a linear or branched alkyl radical comprising from 1 to 12 carbon atoms;
c is an integer ranging from 1 to 500 approximately;
d is an integer ranging from 1 to 500 approximately;
m is an integer ranging from 2 to 12 and preferably from 2 to 5;
s is an integer ranging from 1 to 50 approximately and preferably from 1 to 30;
t is an integer ranging from 0 to 50 approximately and preferably from 0 to 30;
with the proviso that the sum s+t is greater than or equal to 1.

Among these preferential dimethicone copolyol emulsifiers of formula (II), use will particularly be made of PEG-18/PPG-18 dimethicone and more particularly the mixture cyclopentasiloxane (and) PEG-18/PPG-18 dimethicone (INCI name), such as the product sold by the company Dow Corning under the trade name Silicone DC5225 C or KF-6040 from the company Shin-Etsu.

According to a particularly preferred form, use will be made of a mixture of at least one emulsifier of formula (I) and of at least one emulsifier of formula (II).

Use will be made more particularly of a mixture of PEG-18/PPG-18 dimethicone and cetyl PEG/PPG-10/1 dimethicone and even more particularly a mixture of (cyclopentasiloxane (and) PEG-18/PPG-18 dimethicone) and of cetyl PEG/PPG-10/1 dimethicone and dimethicone or of (polyglyceryl-4-stearate and cetyl PEG/PPG-10 (and) dimethicone (and) hexyl laurate).

Among the water-in-oil emulsifiers, mention may also be made of nonionic emulsifiers derived from fatty acids and polyols, alkylpolyglycosides (APGs), sugar esters and mixtures thereof.

As nonionic emulsifiers derived from fatty acids and polyol, use may be made especially of fatty acid esters of polyol, the fatty acid especially containing a $C_8$-$C_{24}$ alkyl chain, and the polyols being, for example, glycerol and sorbitan. Fatty acid esters of polyols that may especially be mentioned include isostearic acid esters of polyols, stearic acid esters of polyols, and mixtures thereof, in particular isostearic acid esters of glycerol and/or sorbitan.

Stearic acid esters of polyols that may especially be mentioned include the polyethylene glycol esters, for instance PEG-30 dipolyhydroxystearate, such as the product sold under the name Arlacel P135 by the company ICI.

Examples of glycerol and/or sorbitan esters that may be mentioned include polyglyceryl isostearate, such as the product sold under the name Isolan GI 34® by the company Evonik Goldschmidt, sorbitan isostearate, such as the product sold under the name Arlacel 987 by the company ICI, sorbitan glyceryl isostearate, such as the product sold under the name Arlacel 986 by the company ICI, the mixture of sorbitan isostearate and polyglyceryl isostearate (3 mol) sold under the name Arlacel 1690 by the company Uniqema, and mixtures thereof.

The emulsifier may also be chosen from alkylpolyglycosides with an HLB 15 of less than 7, for example those represented by the general formula (1) below:

in which:
R represents a branched and/or unsaturated alkyl radical comprising from 14 to 24 carbon atoms;
G represents a reduced sugar comprising from 5 to 6 carbon atoms; and
x denotes a value ranging from 1 to 10 and preferably 1 to 4.

G especially denotes glucose, fructose or galactose.

The unsaturated alkyl radical may comprise one or more ethylenic unsaturations, and in particular one or two ethylenic unsaturations.

As alkylpolyglycosides of this type, mention may be made of alkylpolyglucosides (G=glucose in formula (1)), and especially the compounds of formula (1) in which R more particularly represents an oleyl radical (unsaturated $C_{18}$ radical) or isostearyl (saturated $C_{18}$ radical), G denotes glucose, x is a value ranging from 1 to 2, especially isostearyl glucoside or oleyl glucoside, and mixtures thereof.

This alkylpolyglucoside may be used as a mixture with a coemulsifier, more especially with a fatty alcohol and especially a fatty alcohol containing the same fatty chain as that of the alkylpolyglucoside, i.e. comprising from 14 to 24 carbon atoms and containing a branched and/or unsaturated chain, for example isostearyl alcohol when the alkylpolyglucoside is isostearyl glucoside, and oleyl alcohol when the alkylpolyglucoside is oleyl glucoside, optionally in the form of a self-emulsifying composition, as described, for example, in WO-92/06778.

Use may be made, for example, of the mixture of isostearyl glucoside and isostearyl alcohol, sold under the name Montanov WO 18 by the company SEPPIC, and also the mixture octyldodecanol and octyldodecyl xyloside sold under the name Fludanov 20X by the company SEPPIC.

Mention may also be made of succinic-terminated polyolefins, for instance esterified succinic-terminated polyisobutylenes and salts thereof, especially the diethanolamine salts, such as the products sold under the names Lubrizol 2724, Lubrizol 2722 and Lubrizol 5603 by the company Lubrizol or the commercial product Chemcinnate 2000.

Among the water-in-oil emulsifiers, mention may also be made of oxyalkylenated, especially polyoxyethylenated and/or polyoxypropylenated and more particularly polyoxyethylenated, silicone elastomers such as those described in documents U.S. Pat. Nos. 5,236,986, 5,412,004, 5,837,793 and 5,811,487.

The polyoxyalkylenated silicone elastomer is preferably conveyed in the form of a gel in at least one hydrocarbon-based oil and/or one silicone oil. In these gels, the polyoxyalkylenated elastomer is often in the form of nonspherical particles.

As polyoxyethylenated silicone elastomers, use may be made of those sold by the company Shin-Etsu under the names:
KSG-21 (containing 27% active material, INCI name: Dimethicone/PEG-10 dimethicone vinyl dimethicone crosspolymer);
KSG-20 (containing 95% active material, INCI name: PEG-10 Dimethicone Crosspolymer);
KSG-30 (containing 100% active material, INCI name: Lauryl PEG-15 dimethicone vinyl dimethicone crosspolymer);
KSG-31 (containing 25% active material, INCI name: Lauryl PEG-15 dimethicone vinyl dimethicone crosspolymer);
KSG-32 or KSG-42 or KSG-320 or KSG-30 (containing 25% active material, INCI name: Lauryl PEG-15 dimethicone vinyl dimethicone crosspolymer);
KSG-33 (containing 20% active material);
KSG-210 (containing 25% active material, INCI name: Dimethicone/PEG-10/15 Crosspolymer);
KSG-310: lauryl-modified cross linked polyoxyethylenated polydimethylsiloxane in mineral oil;
KSG-330;
KSG-340;
KSG-226146 (containing 32% active material, INCI name: Dimethicone/PEG-10 dimethicone vinyl dimethicone crosspolymer);
or those sold by the company Dow Corning under the names:
DC9010 (containing 9% active material, INCI name: PEG-12 dimethicone crosspolymer);
DC9011 (containing 11% active material).

These products are generally provided in the form of oily gels containing silicone elastomer particles.

Use is preferably made of KSG-210 (INCI name: Dimethicone/PEG-10/15 crosspolymer), which contains 25% silicone elastomer active material in silicone oil.

Among the water-in-oil emulsifiers, mention may also be made of polyglycerolated silicone elastomers. Such elastomers are especially described in WO 2004/024 798.

Polyglycerolated silicone elastomers that may be used include those sold under the names:

KSG-710 (containing 25% active material, INCI name: Dimethicone/polyglycerine-3 crosspolymer);
KSG-810;
KSG-820;
KSG-830;
KSG-840, sold by the company Shin-Etsu.

Antiperspirant Active Agent

According to a particular embodiment, the composition according to the invention, especially in stick or aerosol form, may also comprise at least one antiperspirant active agent.

The term "antiperspirant active agent" means a salt which, by itself, has the effect of reducing the flow of sweat, of reducing the sensation on the skin of moisture associated with human sweat or of masking human sweat.

The cosmetic composition may in particular comprise one or more antiperspirant active agents chosen from aluminum and/or zirconium salts or complexes.

Among the aluminum salts or complexes, mention may be made of aluminum halo hydrates.

Among the aluminum salts, mention may in particular be made of aluminum chlorohydrate, aluminum chlorohydrex, the aluminum chlorohydrex-polyethylene glycol complex, the aluminum chlorohydrex-propylene glycol complex, aluminum dichlorohydrate, the aluminum dichlorohydrex-polyethylene glycol complex, the aluminum dichlorohydrex-propylene glycol complex, aluminum sesquichlorohydrate, the aluminum sesquichlorohydrex-polyethylene glycol complex, the aluminum sesquichlorohydrex-propylene glycol complex, aluminum sulfate buffered with sodium aluminum lactate.

Aluminum sesquichlorohydrate is especially sold under the trade name Reach 301® by the company SummitReheis.

Aluminum chlorohydrate is in particular sold under the trade names Locron S FLA®, Locron P and Locron L.ZA by the company Clariant; under the trade names Microdry Aluminum Chlorohydrate®, Micro-Dry 323®, Chlorhydrol 50, Reach 103 and Reach 501 by the company SummitReheis; under the trade name Westchlor 200® by the company Westwood; under the trade name Aloxicoll PF 40® by the company Guilini Chemie; Cluron 50%® by the company Industria Quimica Del Centro; or Clorohidroxido Aluminio SO A 50%® by the company Finquimica.

Use will be made more particularly of aluminum chlorohydrate, aluminum aluminum sesquichlorohydrate, and mixtures thereof.

The aluminum salts or complexes may be present in the composition according to the invention in a content ranging from 0.2% to 50% by weight, preferably in a content ranging from 1% to 20% and more particularly between 2% and 15% by weight relative to the total weight of the composition as oils.

Preferably, a composition according to the invention comprises less than 2% by weight of aluminum salts or complexes, more preferentially less than 1% by weight of aluminum salts or complexes and better still less than 0.5% by weight of aluminum salts or complexes relative to the total weight of the composition.

Preferably, a composition according to the invention is free of aluminum salts or complexes.

Propellant

When the composition according to the invention is in aerosol form, it may comprise one or more propellants.

The propellant used in the composition according to the invention is chosen from dimethyl ether, volatile hydrocarbons such as propane, isopropane, n-butane, isobutane, n-pentane and isopentane, and mixtures thereof, optionally with at least one chloro and/or fluoro hydrocarbon. Among the latter, mention may be made of the compounds sold by the company DuPont de Nemours under the names Freon® and Dymel®, and in particular mono fluorotrichloromethane, difluorodichloromethane, tetrafluorodichloroethane and 1,1-difluoroethane, sold in particular under the trade name Dymel 152 A® by the company DuPont.

Carbon dioxide, nitrous oxide, nitrogen or compressed air may also be used as propellant.

Preferably, the composition according to the invention comprises a propellant chosen from volatile hydrocarbons.

More preferentially, the propellant is chosen from isopropane, n-butane, isobutane, n-pentane and isopentane, and mixtures thereof, and is preferably isobutane.

In particular, the weight ratio between the liquid phase and the propellant gas varies in a ratio from 5/95 to 50/50, preferably from 10/90 to 40/60 and more preferentially from 15/85 to 30/70.

Presentation Forms

The compositions according to the invention may be prepared by a person skilled in the art, according to the conventionally known methods.

The compositions may be in liquid, gel, semisolid, solid or loose or compact powder form.

The compositions of the invention may especially be packaged in pressurized form in an aerosol device or in a pump-action bottle; packaged in a device equipped with a perforated wall, especially a grille; packaged in a device equipped with a ball applicator ("roll-on"); packaged in the form of wands (sticks). In this regard, they contain the ingredients generally used in products of this type, which are well known to those skilled in the art.

According to another particular form of the invention, the compositions according to the invention may be solid, in particular in wand or stick form.

In particular, the anhydrous compositions according to the invention are aerosol compositions or are in stick form, and are preferably aerosol compositions.

The term "solid composition" means that the measurement of the maximum force measured by texturometry during the penetration of a probe into the sample of formulation must be at least equal to 0.25 newton, in particular at least equal to 0.30 newton and especially at least equal to 0.35 newton, assessed under precise measurement conditions as follows.

The formulations are poured hot into jars 4 cm in diameter and 3 cm deep. Cooling is performed at room temperature. The hardness of the formulations produced is measured after an interval of 24 hours. The jars containing the samples are characterized in texturometry using a texture analyzer, such as that sold by the company Rheo, TA-XT2, according to the following protocol: a probe of stainless-steel ball type with a diameter of 5 mm is brought into contact with the sample at a rate of 1 mm/s.

The measuring system detects the interface with the sample, with a detection threshold equal to 0.005 newton. The probe penetrates 0.3 mm into the sample, at a speed of 0.1 mm/s. The measuring machine records the change in force measured in compression over time, during the penetration phase. The hardness of the sample corresponds to the average of the maximum force values detected during penetration, over at least three measurements.

The invention also relates to a cosmetic process for treating body odor associated with human perspiration, especially underarm odor, and optionally human perspiration, which consists in applying to the surface of the skin an effective amount of the cosmetic composition as described previously.

The application time of the cosmetic composition to the surface of the skin may range from 0.5 to 10 seconds and preferably from 1 to 5 seconds.

The composition in accordance with the invention may be applied several times to the surface of the skin.

In particular, the cosmetic treatment process according to the invention consists in applying to the surface of the armpits an effective amount of the cosmetic composition as described above.

The invention also relates to the use of said composition for the cosmetic treatment of body odor associated with human perspiration, especially underarm odor, and optionally human perspiration.

Another subject of the present invention is an aerosol device composed of a container comprising an aerosol composition as defined above and of a means for dispensing said composition.

The dispensing means, which forms a part of the aerosol device, generally consists of a dispensing valve controlled by a dispensing head, which itself comprises a nozzle via which the aerosol composition is vaporized. The container containing the pressurized composition may be opaque or transparent. It can be made of glass, of polymer or of metal, optionally covered with a protective lacquer layer.

Throughout the description, including the claims, the term "comprising a" should be understood as being synonymous with "comprising at least one", unless otherwise mentioned.

The expressions "between . . . and . . . ", and "ranging from . . . to . . . " should be understood as meaning limits included, unless otherwise specified.

In the description and the examples, the percentages are percentages by weight, unless otherwise indicated. The percentages are thus given by weight relative to the total weight of the composition. The temperature is expressed in degrees Celsius, unless otherwise mentioned, and the pressure is atmospheric pressure, unless otherwise mentioned.

It is also understood that, unless otherwise mentioned, the contents are expressed relative to the weight of the final composition according to the invention, i.e. taking into account the possible presence of propellant gas.

The invention is illustrated in greater detail by the non-limiting examples presented below.

EXAMPLES

Examples 1 and 2

Two deodorant compositions in aerosol form according to the invention and outside the invention were prepared according to the procedure described below.

The composition of the two formulations is detailed in the table below. The amounts indicated are weight percentages relative to the total weight of the composition.

| Compounds | Trade name | INCI name | Composition 1 (according to the invention) | Composition 2 (outside the invention) |
|---|---|---|---|---|
| Distearyldimethylammonium-modified hectorite | Bentone 38VCG from Elementis | Disteardimonium hectorite | 0.25 | 0.25 |
| Magnesium oxide | Magnesio Oxide Light from Dr Paul Lohmann | Magnesium oxide | 1.5 | 1.5 |
| Refined copra oil | Refined copra oil GV 24/26 from Sio (ADM) | *Cocos nucifera* Oil | 2 | / |
| Fragrance | / | Fragrance | 1.1 | 1.1 |
| polydimethylsiloxane (viscosity: 10 cSt) | Xiameter PMX-200 Silicone Fluid 10 CS from Dow Corning | Dimethicone | 1.5 | 1.5 |
| α,ω-Dihydroxylated polydimethylsiloxane/polydimethylsiloxane mixture 5 cSt; | Xiameter PMX-1503 Fluid from Dow Corning | Dimethicone (and) Dimethiconol | 0.6 | 0.6 |
| Propylene carbonate | Jeffsol propylene from Huntsman | Propylene carbonate | 0.08 | 0.08 |
| Isododecane | Isododecane from Ineos | Isododecane | 3 | 3 |
| Isopropyl palmitate | Isopropyl palmitate from Cognis (BASF) | Isopropyl palmitate | 4.97 | 6.97 |
| Isobutane | / | Isobutane | 85 | 85 |

The composition is prepared by preliminary mixing of the oils with stirring.

The magnesium oxide is then dispersed in the mixture at high shear. The other ingredients are then added at high shear.

Finally, the aerosols are prepared by pressurizing 15 g of composition with 85 g of liquefied isobutane gas.

Results Regarding the Transfer-Resistance Efficacy

Method for evaluating the white marks:

Each of the compositions to be studied is deposited on an imitation leather article sold under the name Supplale® by the company Idemitsu Technofine, which is bonded onto a rigid support. This deposition is performed by spraying the aerosol for 2 seconds at a distance of 15 cm from the support.

The fabric is scanned with a scanner sold under the name Epson V500 Scanner (settings:16-bit grayscale, resolution of 300 dpi).

The transfer evaluation is performed by observation of the residual deposit on the synthetic leather plate.

The aerosols obtained from Example 1 (according to the invention) comprising coconut oil and those obtained from Example 2 (outside the invention) without coconut oil were sprayed under the conditions described above and the results obtained are described in the table below:

| Aerosol | Composition 1 (according to the invention) | Composition 2 (outside the invention) |
|---|---|---|
| Evaluation of white marks | Good | Poor |

The marks obtained with composition 1 according to the invention are much less pronounced than those obtained with composition 2 outside the invention.

Example 3

A deodorant composition according to the invention in stick form was prepared according to the process described below. The composition of this formulation is detailed in the table below. The amounts indicated are weight percentages relative to the total weight of the composition.

| Compounds | Trade name | INCI name | Composition 3 (according to the invention) |
|---|---|---|---|
| Polydimethylsiloxane | Element14 PDMS 10-A from Momentive | Dimethicone | 14 |
| Magnesium oxide | Magnesio Oxide Light from Dr Paul Lohmann | Magnesium oxide | 15 |
| Refined copra oil | Refined copra oil GV 24/26 from Sio (ADM) | *Cocos nucifera* oil | 10 |
| PPG-14 butyl ether | Fluid AP, Low Odor from Amerchol | PPG-14 butyl ether | 10 |
| Isopropyl myristate | Isopropyl myristate from BASF | Isopropyl myristate | 15 |
| Hydrogenated polydecene | Silkflo 366 Polydecene from Ineos | Hydrogenated polydecene | 16 |
| Synthetic wax | Cirebelle 303 from Cirebelle | Synthetic Wax | 5 |
| Polyethylene glycol 400 distearate | PEG 400 distearate (Dub DS PEG 8) from Stearineries Dubois | PEG-8 Distearate | 2.5 |
| Synthetic wax | Cirebelle 108 from Cirebelle | Synthetic Wax | 12 |
| Fragrance | / | Fragrance | 0.5 |

The cyclomethicone is heated to 65° C. The other ingredients are added one by one at a temperature of 65-70° C. The whole is homogenized for 15 minutes.

The mixture is cooled to about 55° C. (a few degrees above the thickening point of the mixture) and is poured into sticks. The whole is maintained at 4° C. for 30 minutes.

The stick obtained produces a dry, non-greasy deposit, while at the same time maintaining good antiperspirant efficacy.

Examples 4 and 5

Two deodorant compositions in aerosol form according to the invention were prepared according to the process described below and compared with composition 2 above outside the invention.

The compositions are detailed in the table below. The amounts indicated are weight percentages relative to the total weight of the composition.

| Trade name | INCI name | Composition 4 (according to the invention) | Composition 5 (according to the invention) |
|---|---|---|---|
| Bentone 38VCG from Elementis | Disteardimonium hectorite | 0.25 | 0.25 |
| Magnesio Oxide Light from Dr Paul Lohmann | Magnesium oxide | 1.5 | 1.5 |
| Pharmaceutical castor oil | Ricinus communis (Castor) Seed Oil | 2 | / |
| Virgin biological sweet almond oil | Prunus amygdalus duclis (Sweet Almond) Oil | / | 2 |
| / | Fragrance | 1.1 | 1.1 |
| Xiameter PMX-200 Silicone Fluid 10 CS from Dow Corning | Dimethicone | 1.5 | 1.5 |
| Xiameter PMX-1503 Fluid from Dow Corning | Dimethicone (and) Dimethiconol | 0.6 | 0.6 |
| Jeffsol propylene from Huntsman | Propylene carbonate | 0.08 | 0.08 |
| Isododecane from Ineos | Isododecane | 3 | 3 |
| Isopropyl palmitate from Cognis (BASF) | Isopropyl palmitate | 4.97 | 4.97 |
| / | Isobutane | 85 | 85 |

The composition is prepared by preliminary mixing of the oils with stirring.

The magnesium oxide is then dispersed in the mixture at high shear. The other ingredients are then added at high shear.

Finally, the aerosols are prepared by pressurizing 15 g of composition with 85 g of liquefied isobutane gas.

Results regarding the transfer-resistance efficacy:

Each of the compositions is evaluated according to the method for evaluating white marks detailed above in Examples 1 and 2.

The aerosols obtained from Examples 4 and 5 (according to the invention) comprising an oil required according to the invention and those obtained from Example 2 (outside the invention) without oil required according to the invention were sprayed under the conditions described previously and the results obtained are described in the table below:

| Aerosol | Composition 4 (according to the invention) | Composition 5 (according to the invention) | Composition 2 (outside the invention) |
|---|---|---|---|
| Evaluation of white marks | Good | Good | Poor |

The marks obtained with compositions 4 and 5 according to the invention are much less pronounced than those obtained with composition 2 outside the invention.

The invention claimed is:

1. An anhydrous composition,
wherein the composition is in the form of an aerosol composition, comprising:
from 0.3% to 5% by weight of active material of magnesium salt(s) relative to the total weight of the aerosol composition;
from 1% to 30% by weight of at least one hydrocarbon plant oil relative to the total weight of the aerosol composition, wherein the at least one hydrocarbon plant oil is selected from the group consisting of liquid triglycerides of fatty acids containing 4 to 24 carbon atoms, wheatgerm oil, olive oil, sweet almond oil, palm oil, rapeseed oil, coconut oil, cottonseed oil, alfalfa oil, poppy oil, pumpkin oil, marrow oil, blackcurrant oil, evening primrose oil, millet oil, barley oil, quinoa oil, rye oil, safflower oil, candlenut oil, passionflower oil, musk rose oil, sunflower oil, corn oil, soybean oil, grapeseed oil, sesame seed oil, hazelnut oil, apricot oil, macadamia oil, castor oil, avocado oil, caprylic/capric acid triglycerides, jojoba oil, shea butter oil, and mixtures thereof; and
from 1% to 30% by weight of at least one fatty acid ester relative to the total weight of the aerosol composition, wherein the at least one fatty acid ester is chosen from isopropyl palmitate, isopropyl myristate, isonorryl isononanoate and $C_{12}$-$C_{15}$ alkyl benzoate, and mixtures thereof, or wherein the composition is in the form of a stick composition, comprising:
from 5% to 25% by weight of active material of magnesium salt(s) relative to the total weight of the stick composition;
from 1% to 30% by weight of at least one hydrocarbon plant oil relative to the total weight of the stick composition. wherein the at least one hydrocarbon plant oil is selected from the group consisting of liquid triglycerides of fatty acids containing 4 to 24 carbon atoms, wheatgerm oil, olive oil, sweet almond oil, palm oil, rapeseed oil, coconut oil, cottonseed oil, alfalfa oil, poppy oil, pumpkin oil, marrow oil, blackcurrant oil, evening primrose oil, millet oil, barley oil, quinoa oil, rye oil, safflower oil, candlenut oil, passionflower oil, musk rose oil, sunflower oil, corn oil, soybean oil, grapeseed oil, sesame seed oil, hazelnut oil, apricot oil, macadamia oil, castor oil, avocado oil, caprylic/capric acid triglycerides, jojoba oil, shea butter oil, and mixtures thereof, and
from 1% to 30% b weight of at least one fatty acid ester relative to the total weight of the stick composition, wherein the at least one fatty acid ester is chosen from isopropyl palmitate, isopropyl myristate, isononyl isononanoate and $C_{12}$-$C_{15}$ alkyl benzoate, and mixtures thereof,
wherein the aerosol composition and the stick composition are in the form of a. deodorant,
wherein the aerosol composition and the stick composition are free of aluminum salts or aluminum complexes, and wherein the at least one hydrocarbon plant oil is/are present in the aerosol composition and the stick composition in an amount ranging from 10% to 90% by weight relative to the total weight amount of oil present, respectively, in the aerosol composition and the stick composition.

2. The aerosol composition or the stick composition as claimed in claim 1, wherein the magnesium salt(s) is chosen from magnesium oxide, magnesium carbonate, magnesium hydroxide and magnesium bicarbonate.

3. The aerosol composition or the stick composition as claimed in claim 1, wherein the magnesium salt(s) is magnesium oxide.

4. The aerosol composition as claimed in claim 1, wherein the magnesium salt(s) are present in a content ranging from 0.5% to 2% by weight of active material relative to the total weight of the aerosol composition.

5. The stick composition as claimed in claim 1, wherein the magnesium salt(s) are present in a content ranging from 10% to 20% by weight relative to the total weight of the stick composition.

6. The aerosol composition or the stick composition as claimed in claim 1, comprising from 1% to 20% by weight of the at least one hydrocarbon plant oil, relative to the total weight respectively of the aerosol composition or the stick composition.

7. The aerosol composition or the stick composition as claimed in claim 1, wherein the at least one hydrocarbon plant oil is coconut oil.

8. The aerosol composition or the stick composition as claimed in claim 1, wherein the at least one fatty acid ester is chosen from isopropyl palmitate, isopropyl myristate, isononyl isononanoate and $C_{12}$-$C_{15}$ alkyl benzoate, and mixtures thereof.

9. The aerosol composition or the stick composition as claimed in claim 1, wherein the at least one fatty acid ester is isopropyl palmitate.

10. The aerosol composition or the stick composition as claimed in claim 1, comprising from 2% to 20% by weight of the at least one fatty acid ester relative to the total weight respectively of the aerosol composition or the stick composition.

11. The aerosol composition as claimed claim 1, comprising at least one volatile oil.

12. The aerosol composition as claimed in claim 1, comprising at least one propellant.

13. The aerosol composition or the stick composition as claimed in claim 7, wherein the at least one fatty acid ester is isopropyl palmitate.

14. The aerosol composition or the stick composition as claimed in claim 3, wherein the at least one hydrocarbon plant oil is coconut oil.

15. The aerosol composition or the stick composition as claimed in claim 3, wherein the at least one fatty acid ester is isopropyl palmitate.

16. The aerosol composition or the stick composition as claimed in claim 14, wherein the at least one fatty acid ester is isopropyl palmitate.

17. A process for the cosmetic treatment of body odor associated with human perspiration, comprising applying the aerosol composition or the stick composition as claimed in claim 1 to a skin surface.

18. The aerosol composition or the stick composition as claimed in claim 1, comprising from 1% to 15% by weight of the at least one hydrocarbon plant oil relative to the total weight respectively of the aerosol composition or the stick composition.

19. The aerosol composition or the stick composition as claimed in claim 1, wherein the at least one hydrocarbon plant oil is chosen from castor oil, sweet almond oil, coconut oil, and mixtures thereof.

20. The aerosol composition or the stick composition as claimed in claim 1, comprising from 3% to 15% by weight of the at least one fatty acid ester relative to the total weight respectively of the aerosol composition or the stick composition.

* * * * *